United States Patent [19]

Joyner

[11] Patent Number: 4,873,998

[45] Date of Patent: Oct. 17, 1989

[54] SURGICAL HAND PROTECTOR SYSTEM

[75] Inventor: Danny W. Joyner, Erwinna, Pa.

[73] Assignee: Johnson & Johnson Patient Care, Inc., New Brunswick, N.J.

[21] Appl. No.: 260,630

[22] Filed: Oct. 21, 1988

[51] Int. Cl.[4] ............................................. A61F 13/00
[52] U.S. Cl. .................................... 128/879; 128/880; 2/16
[58] Field of Search ................................ 128/878–880; 2/16, 20, 21, 158, 159, 161 R, 162, 163, 168

[56] References Cited

U.S. PATENT DOCUMENTS

| | | | |
|---|---|---|---|
| 667,338 | 2/1901 | Rogers | 128/880 |
| 804,406 | 11/1905 | Hungad | 2/21 |
| 1,916,921 | 7/1933 | Dougan | 2/21 |
| 2,072,683 | 3/1937 | Niedorff | 128/880 |
| 2,288,840 | 7/1942 | Raiche | 2/168 |
| 2,845,628 | 8/1958 | Dell | 2/20 |
| 3,084,686 | 4/1963 | Perconti | 128/879 |
| 3,164,841 | 1/1965 | Burtoff | 2/16 |
| 3,606,614 | 9/1971 | Dimitroff | 2/20 |
| 3,890,649 | 6/1975 | Diggins | 2/16 |
| 4,183,100 | 1/1980 | De Marco | 2/159 |
| 4,754,499 | 7/1988 | Pirie | 2/20 |
| 4,785,478 | 11/1988 | Mosley | 2/161 R |

Primary Examiner—Robert A. Hafer
Assistant Examiner—Charles H. Sam
Attorney, Agent, or Firm—Paul A. Coletti

[57] ABSTRACT

A protective surgical hand covering having a hardened molded material placed over the hand. The material will cover the meat of the palm, the knuckles, the lower knuckles, and breadth of the palm. Thimble shaped tips are also available for use. Surgical latex gloves may be worn either over or under the invention.

3 Claims, 1 Drawing Sheet

SURGICAL HAND PROTECTOR SYSTEM

FIELD OF THE INVENTION

This invention relates generally to surgical coverings for protection of the hand. Specifically, this invention relates to hardened plastic coverings for protection of the hand during surgery. Most specifically, this invention relates to hardened plastic coverings for protection of the hand during surgery while permitting flexibility and dexterity of the hand during surgery.

BACKGROUND OF THE INVENTION

By its very nature, surgery can expose the surgeon to injury. When the surgeon dissects, sutures, staples or removes tissue, the surgeon will necessarily be using his hands within close quarters and near cutting instruments. Naturally, because the hands are working within tight constraints, there is the likelihood of their being subjected to these surgical cutting instruments during surgery. This is far more likely to occur within close constraints than during cutting in an open environment. Naturally, because the patient may be infected with viruses or bacteria, these hands may encounter these germs internally upon piercing by the surgical instrument.

For this reason, surgeons have worn protective coverings on their hands. These protective coverings must possess two necessary characteristics. First, the protective covering must be rigid to actually protect the hand from being cut during surgery. Conversely, the protective covering must also permit a wide range of flexibility and dexterity, to allow the surgeon to perform surgical procedures.

This combination has been quite difficult to achieve. The generally thin pliable latex gloves commonly worn by surgeons allow for a high degree dexterity, but are quite thin. These latex gloves generally will not withstand piercing by instruments such as surgical scalpels. This is especially true concerning areas of the hand more subject to piercing by surgical instruments, such as the back of the hand near the knuckles and the meat of the palm generally below the thumb. Thus, while these latex gloves will afford some protection, especially from allowing the skin to contact blood during surgery, these surgical gloves will not insure against self-wounding by the surgeon.

SUMMARY OF THE INVENTION

It is therefore an object of the invention to protect the hands during surgery.

It is a further object of the invention to protect the hands during surgery while permitting flexibility and dexterity of the fingers necessary during surgical procedures.

Finally, it is yet another object of the present invention to protect the hands during surgery while permitting latex gloves to be worn on the hands in order to prevent contact with bacteria by the hands during surgery.

These and other objects of the present invention are accomplished in a protective surgical hand covering which allows the surgeon to have both dexterity and protection. The surgical hand covering generally comprises a hardened plastic material which forms a continuous band around the areas of the hand more susceptible to injury. These generally will comprise the lower knuckles on the back of the hand and the meat of the palm. The surgical hand covering will be emplaced over the fingers through holes made in the covering. The covering will become seated on the fingers and will protect the lower part of the hand. This will allow surgeons to be able to cut without injuring the back of the hand. It also prevents needles from sticking the meat of the palm during surgery.

The molded plastic material from which the protective hand covering is made also will allow the surgeon to wear latex gloves under the hand covering. This will protect the hands from bacteria and viruses during surgery, for instance when the surgeon enters the open body cavity with his hands. Conversely, the present invention can be slipped onto the hands and latex gloves can be placed over the protective hand covering.

Finally, the protective hand covering also discloses thimble-like tips which may be fitted over the tops of the fingers. These tips can be attached to the continuous band by means of narrow fibers that will continue to allow the surgeon to have dexterity during surgery.

These and other aspects of the invention will be better understood from the following description of the drawings when taken in conjunction with the detailed description of the invention in which:

DETAILED DESCRIPTION OF THE INVENTION

Figure 1:
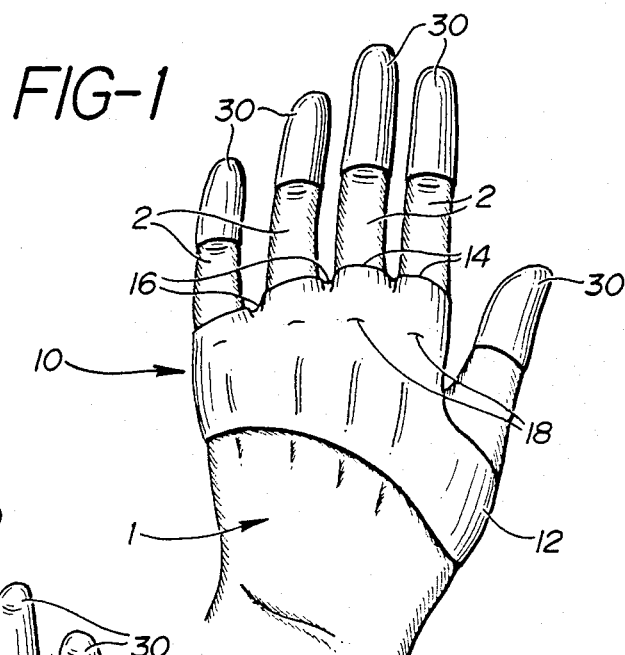
FIG. 1 is a top plan view of the preferred embodiment of the present invention placed on the hand.
Figure 2:
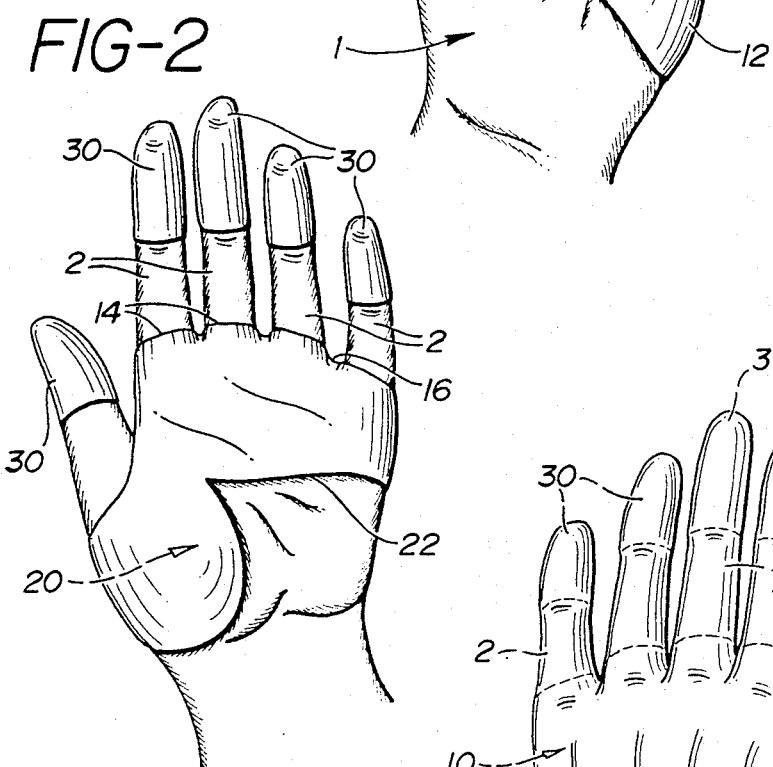
FIG. 2 is a bottom plan view of the preferred embodiment of the present invention when placed on the hand.

As seen in FIGS. 1 and 2, the protective covering 10 of the present invention comprises a hardened plastic band 12. This hardened plastic band 12 is generally made out of a thermoplastic material, which must have substantial density and yet allow enough flexibility to move the hand. The molded plastic band 12 comprises fingers 14. These fingers 14 are formed having webs 16, although it is, of course, understood that webs 16 are not necessary for protection of the knuckles or the back of the hands. The fingers 14 have openings in them for emplacement of the fingers 2 of the hand 1.

The back of the protective band 12 is shaped so that it will cover the knuckles 18. The knuckles 18 are formed into the band to allow it to properly cover the hand. Turning to FIG. 2, it is seen that the meat of the palm 20 is also covered, formed as an extension of the continuous band 12. The remainder of the palm is cut from the protective covering 10 as seen by rectangular cut out 22.

Thimble shaped tips 30 may be emplaced over the tips of the fingers 2 of the hand 1 as seen in FIGS. 1 and 2. These thimble shaped tips 30 are formed to the size of the fingers 2. These thimble shaped tips 30 allow covering of the fingers 2, especially on the nondominant surgical hand, where a larger degree of dexterity is not necessary. These thimble shaped tips 30 may be connected to the protective band 12 by means of fibers extending from the tips 30 to the fingers 14 of the protective band 12. Alternately, these tips 30 may extend for the length of the fingers 2.

Figure 3:
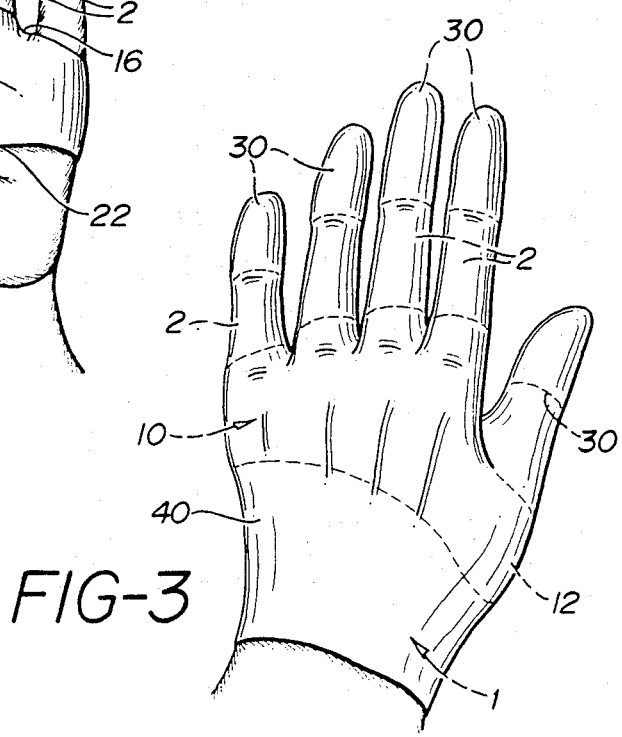
FIG. 3 is a top plan view of the preferred embodiment of the present invention with latex gloves placed over the invention.

Finally, as seen in FIGS. 3, this protective covering 10 may be placed on the hand so that a latex glove can be emplaced either over or under the protective covering 10. The protective surgical hand covering 10 has been emplaced on the hand 1, and then a latex glove 40 has been emplaced over the entire combination. Alternately, the surgeon may first place a latex glove 40 on the hand 1, and then emplace the continuous band 12 and the thimble shaped tips 30 of the protective surgical hand covering over the latex glove 40.

When in use, therefore, the protective surgical hand covering 10 of the present invention uniquely combines the two objectives for the surgeon. First because the plastic is pliable enough, it permits dexterity of the hand. This is especially true of the nondominant surgical hand, where dexterity is not an imposing factor. Because the fingers of the hand are allowed freedom of motion, the hand is generally able to grip and hold various surgical objects. Yet, because the protective surgical hand covering 10 is made of a hardened thermoplastic, it permits greater protection of the hand from cuts by surgical instruments. Thus, the surgeon is now less susceptible to injury during surgery.

The present invention has been described in conjunction with the preferred embodiment. Those skilled in the art will appreciate that many modifications and changes may be made to the preferred embodiment without departing with the present invention. It is therefore not intended to limit the present invention except as set forth in the appended claims.

What is claimed is:

1. A surgical hand protector system comprising:

- a molded thermoplastic band for emplacement over the base of the hand, said band forming a continuous loop to rest between the thumb and index finger of the hand and around the palm and back of the hand, said band containing performations into which can be placed the fingers;
- a molded projection connected to said band and formed from the same thermoplastic material as said band, said projection covering a portion of the thumb and containing a perforation through which can be placed the thumb;
- said band and said projection having continuous open ends through which the hand is insertable, said band and said projection forming an open portion which exposes a part of the palm below the third and fourth fingers to allow greater dexterity during use of said system; and
- a pliable surgical glove emplaced over the hand to cover the areas of the hand exposed by said band and said projection;
- wherein the hand is completely covered yet retains dexterity and mobility when protected by said system.

2. The surgical hand protector system of claim 1 further including thermoplastic tips fitted over the tops of the fingers and the thumb, said tips connected to said continuous band by means of threads attached to said tips and said band.

3. The surgical hand protector system of claim 1 further including thermoplastic tips fitted over the tops of the fingers of the hand.

* * * * *